United States Patent [19]

Bailey

[11] Patent Number: 4,870,095

[45] Date of Patent: Sep. 26, 1989

[54] 1H-PYRAZOLE-1-ALKANAMIDES, ANTIARRHYTHMIC COMPOSITIONS AND USE

[75] Inventor: Denis M. Bailey, East Greenbush, N.Y.

[73] Assignee: Sterling Drug, Inc., New York, N.Y.

[21] Appl. No.: 327,226

[22] Filed: Mar. 22, 1989

Related U.S. Application Data

[63] Continuation-in-part of Ser. No. 206,246, Jun. 13, 1988, which is a continuation-in-part of Ser. No. 72,490, Jul. 13, 1987, abandoned.

[51] Int. Cl.⁴ ............... A61K 31/415; C07D 231/12; C07D 231/20
[52] U.S. Cl. .................... 514/406; 514/212; 514/326; 514/404; 540/603; 546/211; 548/363; 548/364; 548/367; 548/374; 548/378
[58] Field of Search .............. 540/603; 546/211; 548/363, 364, 367, 374, 378; 514/212, 326, 404, 406

[56] References Cited

U.S. PATENT DOCUMENTS

| | | |
|---|---|---|
| 4,072,498 | 2/1978 | Moon et al. ............... 71/92 |
| 4,182,895 | 1/1980 | Bailey ...................... 548/378 |
| 4,695,566 | 9/1987 | Heinemann et al. ........ 548/369 |

Primary Examiner—Robert W. Ramsuer
Attorney, Agent, or Firm—Philip E. Hansen; Paul E. Dupont

[57] ABSTRACT

N-[(disubstituted amino)alkyl]-3,4 (or 4,5)-diaryl-1H-pyrazole-1-acetamides and pyrazole-1-propanamides, useful for treating cardiac arrhythmias in mammals, are prepared by reacting a lower-alkyl ester of pyrazole-1-acetic or propanoic acid with an appropriate diamine or by reacting a lower-alkyl ester of a pyrazole-1-acetic or propanoic acid with an ω-aminoalkanol, followed by activation of the alcohol and displacement by an appropriate amine.

31 Claims, No Drawings

1H-PYRAZOLE-1-ALKANAMIDES, ANTIARRHYTHMIC COMPOSITIONS AND USE

RELATED APPLICATIONS

This is a continuation-in-part of my prior copending application Ser. No. 206246, filed June 13, 1988, which is a continuation-in-part of application Ser. No. 072490, filed July 13, 1987, now abandoned.

BACKGROUND OF THE INVENTION

1. Field of the Invention

The present invention relates to novel N-[(alkyl amino)alkyl]-3,4 (or 4,5)-diaryl 1H-pyrazole-1-acetamides or propanamides, processes for the synthesis of said pyrazole-1-alkanamides, and methods for treating cardiac arrhythmia in mammals utilizing said pyrazole-1-alkanamides.

2. Information Disclosure Statement

U.S. Pat. No. 4,695,566 to Heinemann et. al., which is equivalent to German Offenlegungsschrift DE 3424586, published Jan. 9, 1986, discloses as antiarrythmic agents 1H-pyrazol-3-yl (and 1H-pyrazol-5-yl)oxyacetamides of general formula

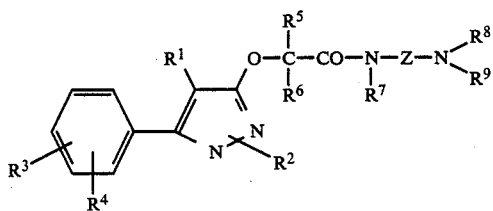

Specifically disclosed are (1) N-[2-(diethylamino)ethyl]-2-[(5-phenyl-1H-pyrazol-3-yl)oxy]acetamide, example 5, and (2) N-[3-(diethylamino)propyl]-2-[(5-phenyl-1H-pyrazol-3-yl)oxy]acetamide, example 24.

My own U.S. Pat. No. 4,182,895, issued Jan. 8, 1980, discloses as an intermediate in the synthesis of 1-amino-lower-alkyl-3,4-diphenyl-1H-pyrazoles "β-[1-(3,4-diphenyl-1H-pyrazolyl)]-N,N-dimethylpropionamide" at column 8, line 63 to 64.

European patent applications 248594, 293220, and 293221 to Ortho Pharmaceutical Corporation describe the synthesis of 1,5-diphenyl-1H-pyrazole-3-alkanoic acids and the use of these acids and their esters as cyclooxygenase and lipoxygenase inhibitors.

Bondavalli et al. [Farmaco, Ed. Sci 43, 725–743 (1988)] disclose N-alkyl carbamates of 1-(2-hydroxyethyl)-3,5-diphenyl-1H-pyrazole as antihypertensive, antiarrhythmic, analgesic, antiinflammatory and hypoglycemic agents. Specifically disclosed are the ethyl, isopropyl, phenyl and 1-naphthyl carbamates.

U.S. Pat. No. 4,072,498 to Moon and Kornis discloses N,N,α,α-tetramethyl-3,4-diphenylpyrazole-1-acetamide as a herbicide (example 160).

SUMMARY OF THE INVENTION

In a product aspect the invention relates to compounds of the formula Ia or Ib

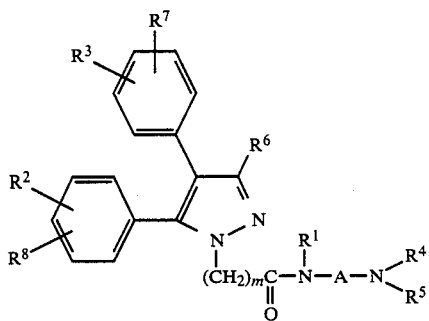

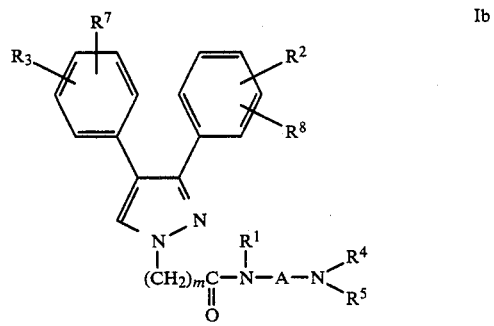

or acid-addition salt thereof wherein $R^1$ is hydrogen or lower-alkyl; $R^2$ and $R^3$ are independently hydrogen, hydroxy, lower-alkyl, lower-alkoxy, lower-alkylamino, lower-alkylamido, lower-alkylsulfonamido, nitro, amino, cyano, or halo; $R^4$ and $R^5$ are independently hydrogen lower-alkyl or hydroxy lower-alkyl or $R^4$ and $R^5$ together form a straight or branched alkylene chain of four to six carbons; $R^6$ is hydrogen or hydroxy; $R^7$ and $R^8$ are independently hydrogen, hydroxy, lower-alkoxy, lower-alkyl, or halo; m is one or two; and A is $CH_2CH(OH)CH_2$ or $(CH_2)_n$ where n is an integer from two to eight.

Lower-alkyl as used herein describes linear or branched hydrocarbon chains of four or fewer carbon atoms; lower-alkoxy as used herein describes linear or branched alkyloxy substituents containing four or fewer carbon atoms; halogen describes bromine, chloride or fluorine.

In a further product aspect, the invention relates to compositions for treating cardiac arrhythmia which comprise compounds of the formula I together with pharmaceutically acceptable excipients or diluents as required.

In a process aspect, the invention relates to a method for treating cardiac arryhthmia in a mammal which comprises administering to said mammal an antiarrhythmically effective amount of a compound of formula I.

Processes are described for preparing a compound of formula I comprise reacting a pyrazole-1-acetate or propanoate with an amine. Further processar for preparing a compound of formula I comprise reacting a 3,4 or 4,5-disubstituted pyrazole-1-acetate or propanoate with an ω-amino linear alkanol, converting the resulting alcohol to a group that is subject to nucleophilic displacement, and displacing said group with an amine.

DETAILED DESCRIPTION INCLUSIVE OF PREFERRED EMBODIMENTS

The synthesis of compounds of the invention may be outlined as shown in scheme A wherein $R^9$ is hydrogen or lower-alkyl.

or secondary amine of formula III at 20° to 150° C., preferably at 90 to 150° C. When the amine is valuable, the ester II is preferably reacted with about one equivalent of the amine III in the presence of a tertiary amine, preferably diisopropylethylamine, in an inert solvent.

Alternatively, the compounds of the invention

Scheme A

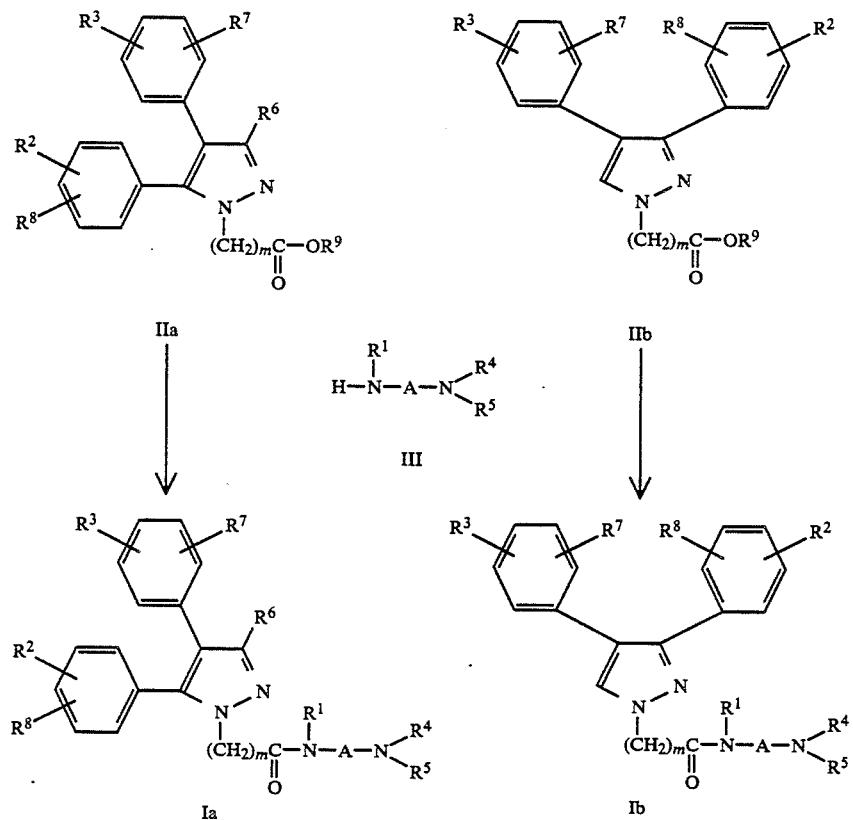

A lower-alkyl ester, preferably a methyl or ethyl ester, of a suitably substituted 3,4- or 4,5-diphenylpyrazole-1-alkanoic acid (II) is reacted with an excess of a primary wherein A is $(CH_2)_n$ may be synthesized as outlined in Scheme B:

Scheme B

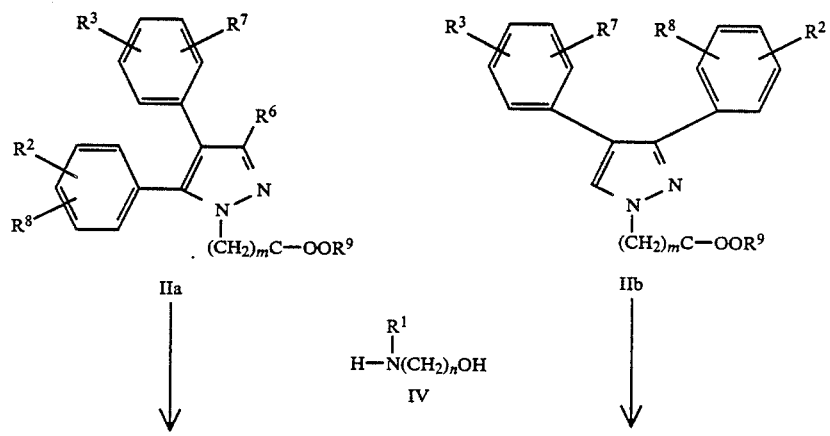

Scheme B

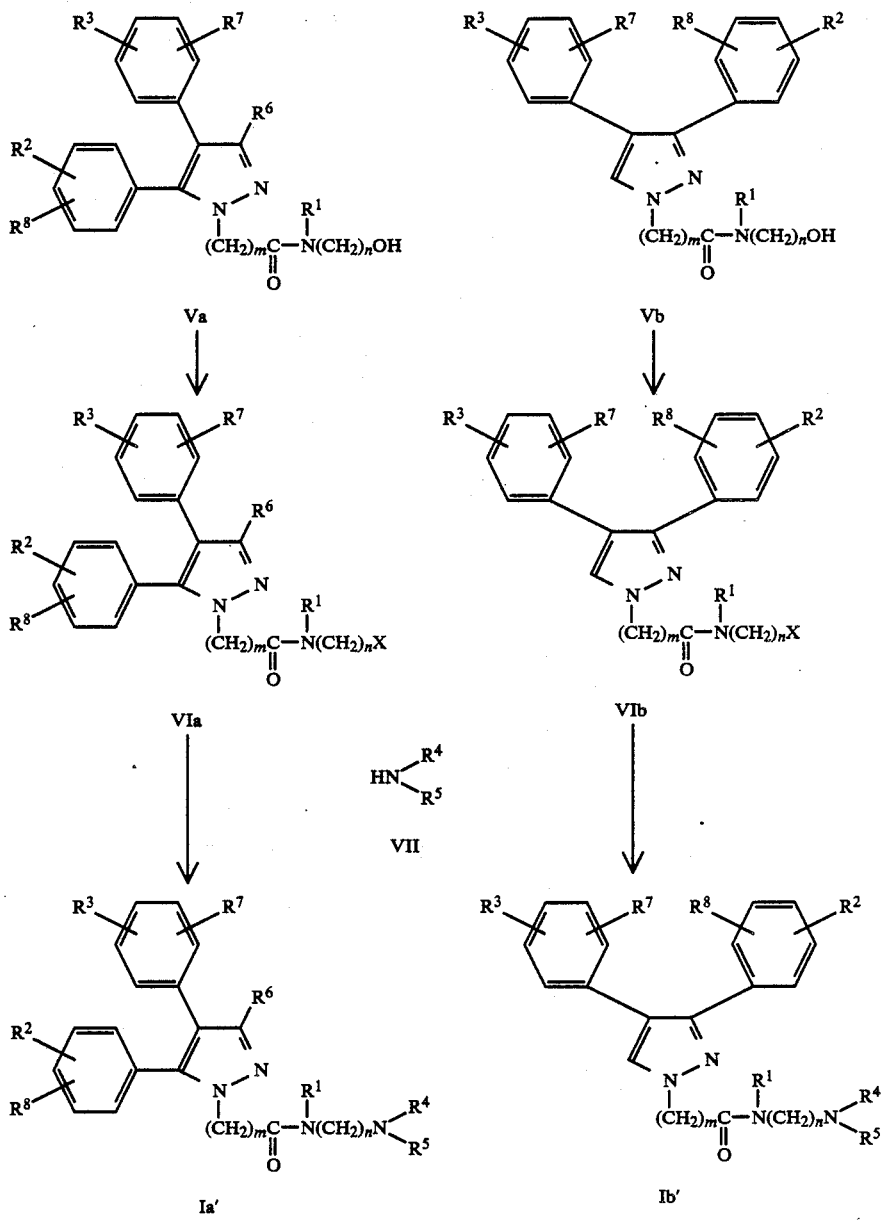

A lower-alkyl ester, preferably a methyl or ethyl ester, of a suitably substituted 3,4- or 4,5-diphenyl-1H-pyrazole-1-alkanoic acid (II) is reacted with an excess of a primary or secondary -aminoalkanol (IV) optionally in the presence of an external base at 20°–150° C., preferably at 90°–100° C. to produce an N-[-hydroxyalkyl[-pyrazole-1-alkanamide of formula V. The hydroxyalkylalkanamide (V) is activated preferably by sufonylation, preferably with methanesulfonyl chloride when $R^6$ is hydrogen or toluenesulfonyl chloride when $R^6$ is hydroxy, in the presence of a base/solvent such as pyridine at −20° to 20° C., preferably at 0° C., to produce an alkylalkanamide of formula VI wherein X is a group which is subject to nucleophilic displacement such as toluenesulfonate or methanesulfonate.

Alternatively when $R^6$ is hydrogen, the hydroxyalkylalkanamide (V) is converted to the corresponding halide (VI, X=Cl, Br or I) by phosphorus trihalide, phosphorus pentahalide, thionyl halide or tetrahalomethane with trialkylphosphine. The group X is then displaced by reaction in the presence or absence of solvent with an appropriate primary or secondary amine (VII) at 20° to 100° C.

The ester IIa where $R^6$ is hydrogen and m is one, or IIb where m is one may be synthesized from the appropriately substituted desoxybenzoin by formylation by means of known procedures [Russell et al J. Am. Chem. Soc. 76, 5714 (1954)] followed by condensation with a hydrazinoacetic acid ester in a suitable solvent, preferably ethanol, at 20° to 100° C., preferably at 25° C. The hydrazinoacetate is preferably used in the form of a mineral acid salt from which the free hydrazine may be liberated in situ by the addition of about one equivalent of a base, preferably pyridine.

Ester IIa where $R_6$ is hydrogen and m is two or IIb where m is two may be synthesized from the appropriately substituted diaryl pyrazole by a two step procedure comprising reaction with acrylonitrile in the presence of base in an inert solvent at 0°-50° C., preferably at about 20° C., followed by hydroylsis of the nitrile using methanol and hydrogen chloride in an inert solvent at 0° to 30° C. and then water at 0°-30° C.

When only the 4,5-diphenyl isomer of the products of formula Ia where m is one and $R^6$ is hydrogen is desired, the 4,5-diphenyl ester IIa where $R^6$ is hydrogen may be synthesized from the appropriately substituted desoxybenzoin by a two-step procedure comprising reaction with N,N-dimethylformamide dimethyl acetal in an inert solvent, preferably methyl tert-butyl ether, at 20°-100° C. preferably at about 55° C., followed by cyclization with a lower-alkyl ester of hydrazinoacetic acid as described above.

Other processes for the production of ester IIa where $R^6$ is hydrogen and m is two or IIb where m is two, as well as a detailed description of the determination of the identity of particular isomers, are described in U.S. Pat. No. 4,182,895.

The ester IIa where $R^6$ is hydroxy may be synthesized from the appropriate 3,4-diphenyl-5-pyrazolone by alkylation with an ω-haloalkanoate in the presence of about one equivalent of a base, preferably potassium carbonate, in an inert solvent at 20°-100° C., preferably at about 55° C.

The compounds of formulas Ia and Ib are useful both in the free base form and in the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts that is, salts whose anions are relatively innocuous to the animal organism in medicinal doses of the salts so that the benefical properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance, and mass spectroscopy. The course of the reactions and the identity and homogeneity of the products were assessed by thin layer chromatography (TLC) or gas-liquid chromatography (GLC). The starting materials are either commercially available or may be prepared by procedures well known in the art.

In the following procedures melting points are given in degrees C. and are uncorrected. The abbreviation THF stands for tetrahydrofuran, DMF stands for N,N-dimethylformamide and Ac stands for the acetyl residue, $CH_3CO$.

EXAMPLE 1A

Ethyl 4,5-diphenyl-1H-pyrazole-1-acetate

A slurry of 200 g (0.89 mol) of formyldesoxybenzoin and 138 g (0.89 mol) of ethyl hydrazinoacetate hydrochloride in 2 L of ethanol were stirred at room temperature and 72 mL (0.89 mol) of pyridine was added dropwise. The reaction was stirred at room temperature and progress was assessed by periodic TLC using 3% acetic acid, 25% acetone and 72% toluene on silica gel. When, after the addition of a further 3 mL of pyridine over the course of 18 hours, the reaction was judged complete by TLC, the solvent was stripped in vacuo and the residue slurried in ethyl acetate. The ethyl acetate solution was filtered free of solid impurity, washed with water then saturated sodium chloride solution and dried over magnesium sulfate. The ethyl acetate was stripped to a reddish oil which was triturated in pentane to yield 156 g of solid. The product was recrystallized carefully from ether-pentane to yield 44.6 g of ethyl 4,5-diphenyl-1H-pyrazole-1-acetate, mp 79°-81° C. By repeated careful crystallization from ether-pentane a further 99.6 g of the 4,5-diphenyl isomer may be obtained for a total yield of 144.2 g (53% yield).

EXAMPLE 1B

Ethyl 4,5-Diphenyl-1H-pyrazole-1-acetate

When only the 4,5-diphenyl isomer is desired the following procedure is preferred. A mixture of 778 g (3.96 mol) deoxybenzoin, 580 mL (4.38 mol) of N,N-dimethylformamide dimethyl acetal, and 775 mL of methyl tert-butyl ether was refluxed for 3 hours. The reaction mixture was cooled on ice to 0°-5° C. The precipitated solid was collected by filtration, the filter cake washed with 250 mL of cold methyl tert-butyl ether twice and dried in vacuum chamber at 65° C. to afford 913 g (92%) of 3-(dimethylamino)-1,2-diphenyl-2-propen-1-one, mp 128°-133° C. A slurry of 913 g (3.64 mol) of 3-(dimethylamino)-1,2-diphenyl-2-propen-1-one in 3.4 L of absolute ethanol was treated with 618 g (4 mol) of ethyl hydrazinoacetate hydrochloride in one portion. The mixture was stirred at room temperature for 1 hour, filtered through diatomaceous earth, and the filtrate treated with 7 L of 50% aqueous ethanol with stirring. Cooling of the resultant solution to 0°-5° C. provided a white solid which was collected by filtration, washed with 250 mL of cold 50% ethanol twice and dried in vacuum at 40° C. to provide 970 g (87%) of ethyl 4,5-diphenyl-1H-pyrazole-1-acetate, mp 76°-80° C., containing none of the 3,4-diphenyl isomer detectable by GLC.

EXAMPLE 2

Ethyl 3,4-diphenyl-1H-pyrazole-1-acetate

Chromatography of the mother liquors from Example 1A on silica gel using 1:1 chloroform-hexane provided up to 20% of the 3,4-diphenyl isomer. The 3,4-diphenyl isomer (Example 2) may be distinguished from the 4,5-diphenyl isomer (Example 1) by its higher Rf on TLC. An analytical sample may be obtained by distillation at 0.2 mm, boiling range 186°-189° C.

EXAMPLE 3

Ethyl 4,5-bis(4-fluorophenyl)-1H-pyrazole-1-acetate and ethyl 3,4-bis(4-fluorophenyl)-1H-pyrazole-1-acetate Following the procedure of Example 1, 19.7 g (0.076 mol) of 1,2-bis(4-fluorophenyl)-3-hydroxy-2-propen-1-one, 11.8 g (0.076 mol) of ethyl hydrazinoacetate hydrochloride and 6.3 mL (0.078 mol) of pyridine were reacted at room temperature to produce 19.9 g of the mixed 4,5- and 3,4-diphenyl isomers. The isomers were separated by high pressure liquid chromatography on silica gel eluting with 97% toluene, 3% ethyl acetate. The peak with k'=2.0 yielded 1.8 g of the 3,4-diphenyl isomer, mp 98°-99° C., and the peak with k'=4.0 yielded 11.16 g of the 4,5-diphenyl isomer, mp 83°-84° C.

EXAMPLE 4

Methyl 3,4-diphenyl-1H-pyrazole-1-propanoate and Methyl 4,5-diphenyl-1H-pyrazole-1-propanoate Thirty grams (0.136 mol) of 3,4 (4,5)-diphenylpyrazole and 11.2 mL (0.169 mol) of acrylonitrile were combined in 450 mL of methylene dichloride and 0.56 g (0.01 mol) of sodium methoxide were added. The mixture was heated with stirring under nitrogen for four hours and allowed to stand under nitrogen for 18 hours. The reaction was filtered and evaporated under vacuum below 30° C. The residue was taken up in hot absolute alcohol and cooled. The first crop of 22.7 g of damp solid was shown by NMR to consist of 30% of the 3,4 isomer and 70% of the 4,5 isomer. It was recrystalized a second time from about 350 mL of ethanol to yield 11 g of the pure 4,5 diphenyl isomer, mp 123°-124° C. A second crop of 9 g of damp solid from the first crystalization was shown by NMR to be essentially pure 3,4diphenyl isomer mp 82°-85° C.

In an ice bath under nitrogen, hydrogen chloride gas was passed through a suspension of 100 mg (0.4 mol) of 4,5-diphenylpyrazole-1-propionitrile and 2 mL of dry methanol for 5 to 10 minutes. Since the starting nitrile was not in solution, 2 mL of THF and 2 mL of methanol were added. The mixture was again treated with hydrogen chloride gas. The temperature shot above 20° C. and the hydrogen chloride gas was turned off. The reaction was stirred at room temperature for 48 hours, and 70 mg of crystalline iminoether hydrochloride was filtered off, mp 90°-91° C.

The iminoether hydrochloride was dissolved in 5 mL of methylene chloride, cooled to 0° C., and 10 drops of water were added. The reaction was stirred for a few minutes at 0° C. and then for a few minutes at room temperature. The methylene chloride layer was separated and dried over magnesium sulfate, filtered and evaporated to yield 30 mg of methyl 4,5-diphenyl-1H-pyrazole-1-propanoate, mp 72°-74° C.

EXAMPLE 5

Ethyl 4-(4-methoxyphenyl)-5-phenyl-1H-pyrazole-1-acetate

Following the procedure of example 1B 11 g (0.39 mol) of 3-(dimethylamino)-2-(4-methoxyphenyl)-1-phenyl-2-propene-1-one and 6.6 g (0.43 mol) of ethyl hydrazinoacetate hydrochloride were reacted in 55 mL of absolute methanol under nitrogen. After 1½ hours, 11.2 g of solid product was filtered off, mp 81°-84° C.

EXAMPLE 6

Ethyl 5-(4-hydroxyphenyl)-4-phenyl-1H-pyrazole-1-acetate

Following the procedure of example 1B, 15 g (0.05 mol) of 3-(dimethylamino)-1-(4-hydroxyphenyl)-2-phenyl-2-propene-1-one and 9 g (0.058 mol) of ethyl hydrazino acetate hydrochloride were reacted in 75 mL of absolute ethanol. After 1½ hours, 14.38 g of solid product was filtered off, mp 130°-135° C.

EXAMPLE 7

Ethyl 4-(4-fluorophenyl)-5-phenyl-1H-pyrazole-1-acetate

Following the procedure of example 1B, 13.8 g (0.0645 mol) of 2-(4-fluorophenyl)-1-phenylethanone was reacted with 20 mL of dimethyl formamide dimethyl acetal to yield 13.6 g of 3-(dimethylamino)-2-(4-fluorophenyl)-1-phenyl-2-propen-1-one, mp 115°-116° from isopropyl acetate. The enamine (10.5 g, 0.039 mol) was reacted with 6.03 g (0.039 mol) of ethyl hydrazinoacetate hydrochloride to yield 12.1 g of product mp 86°-87° C. from methyl-t-butyl ether.

EXAMPLE 8

Ethyl 4-(4-nitrophenyl)-5-phenyl-1H-pyrazole-1-acetate

By a procedure analogous to that of example 7, 11.9 g of ethyl 4-(4-nitrophenyl)-5-phenyl-1H-pyrazole-1-acetate, mp 78-79 from methyl t-butyl ether, was synthesized from 17.6 g (0.073 mol) of 2-(4-nitrophenyl)-1-phenylethanone, 35 mL of dimethyl formamide dimethyl acetal and 7.04 g (0.0456 mol) of ethyl hydrazinoacetate hydrochloride.

EXAMPLE 9

Ethyl 4-(4-chlorophenyl)-5-phenyl-1H-pyrazole-1-acetate

By a procedure analogous to that of example 7, 8.5 g of ethyl 4-(4-chlorophenyl)-5-phenyl-1H-pyrazole-1-acetate mp 75°-76° from triethylamine, was synthesized from 11.48 g (0.049 mol) of 2-(4-chlorophenyl)-1-phenylethanone, 12 mL of dimethyl formamide dimethyl acetal and 4.95 g (0.032 mol) of ethyl hydrazinoacetate hydrochloride.

EXAMPLE 10

Ethyl 4-(4-cyanophenyl)-5-phenyl-1H-pyrazole-1-acetate

By a procedure analogous to that of example 7, 6.7 g of ethyl 4-(4-cyanophenyl)-5-phenyl-1H-pyrazole-1-acetate, mp 124°-125° from methyl t-butyl ether, was synthesized from 7.72 g (0.035 mol) of 2-(4-cyanophenyl)-1-phenylethanone, 10 mL of dimethyl formamide dimethyl acetal and 3.7 g (0.024 mol) of ethyl hydrazino-acetate hydrochloride.

The 2-(4-cyanophenyl)-1-phenylethanone was synthesized from 4-cyanobenzyl bromide and ω-cyano-N,N-diethylbenzenemethanamine: 3.95 g (0.16 mol) of sodium hydride was suspended in 80 mL of DMF under nitrogen and 29.9 g (0.16 mol) of the methanamine in 20 mL of DMF was added dropwise. When evolution of hydrogen had ceased, 31.2 g (0.16 mol) of the benzyl bromide in 30 mL of toluene was added and the reaction stirred 3 hr at room temperature. The reaction was stripped, 300 mL of 6N HCL was added and the suspension was stirred 4 hr, let sit 18 hr and extracted with chloroform. The chloroform extract was stripped, dissolved in ethyl acetate, and filtered through silica gel to remove a purple impurity. The ethyl acetate solution was stripped, the residue was triturated in ether and recrystallized from methanol to give 7.72 g of 2-(4-cyanophenyl)-1-phenylethanone, mp 113°–114° C.

EXAMPLE 11

Ethyl 5-[4-(dimethylamino)phenyl]-4-phenyl-1H-pyrazole-1-acetate

By a procedure analogous to that of example 7, 13.7 g of ethyl 5-[4-(dimethylamino)phenyl]-4-phenyl-1H-pyrazole-1-acetate, mp 99°–101° C. from ether, was synthesized from 13.0 g (0.054 mol) of 1-[4-(dimethylamino)phenyl]-2-phenylethanone, 27.6 mL (0.196 mol) of dimethyl formamide dimethyl acetal and 7.9 g (0.05 mol) of ethyl hydrazinoacetate hydrochloride.

EXAMPLE 12

N-[3-(diethylamino)propyl]-4,5-diphenyl-1H-pyrazole-1-acetamide hemihydrate

A. A mixture of 8 g (0.026 mol) of ethyl 4,5-diphenyl-1H-pyrazole-1-acetate (Example) and 40 mL (0.25 mol) of diethylaminopropylamine was heated on a steam bath under nitrogen for 14 hours. The excess diethylaminopropylamine was stripped in vacuo and the residue dissolved in ether. The ether solution was washed two times with water, once with saturated sodium chloride, dried over magnesium sulfate, filtered and evaporated in vacuo. The resulting white residue was dissolved in ether and a small amount of undesired material was removed by filtration after addition of some pentane. The filtrate was stripped, redissolved in ether, dried over magnesium sulfate, treated with decolorizing carbon, filtered and evaporated. The resulting residue was triturated in water, filtered and rinsed with water to yield 8.55 g (82%) of N-[3-(diethylamino)propyl]-4,5-diphenyl-1H-pyrazole-1-acetamide hemihydrate, mp 70°–74° C. The product can be recrystallized from wet ether.

B. The methane sulfonate salt was prepared by dissolving 6 g of the free base in 150 mL of isopropyl alcohol and treating with one equivalent of methanesulfonic acid; mp 166°–168° C.

C. The fumarate salt was prepared by dissolving 70 g of the free base in 250 mL of hot isopropyl alcohol, adding 20.8 g of fumaric acid in 100 mL of methanol, refluxing, filtering, and cooling. There was obtained 83 g of N-[3-(diethylamino)propyl]-4,5-diphenyl-1H-pyrazole-1-acetamide (E)-2-butenedioate (1:1), mp 154°–156° C.

For large scale preparation of N-[3-(diethylamino)propyl]-4,5-diphenyl-1H-pyrazole-1-acetamide (E)-2-butenedioate (1:1) the following procedure was found to be superior: A solution of 2.2 kg (7.3 mol) of ethyl 4,5-diphenyl-1H-pyrazole-1-acetate in 4.3 kg (33 mol) of 3-diethylaminopropylamine was heated at 135°–148° C. for 1.5 hours while distilling off ethanol. Excess amine was removed by vacuum distillation; the residue was dissolved in 6 L of isopropyl acetate and washed twice with 3 L of water. The organic layer was concentrated to a white solid, which was dissolved in 14 L of ethanol, treated with 0.96 kg (8.3 mol) of fumaric acid, and heated to 75° C. to achieve a clear solution. The solid product was obtained by filtration of the cooled solution. The first crop weighed 3.1 kg (84% yield) and melted at 157°–159° C.; a second crop, m.p. 155°–157° C., 0.36 kg (9%) was obtained upon concentration of the mother liquors.

D. The toluenesulfonate salt was prepared by dissolving 70 g of the free base in 250 mL of hot isopropyl alcohol, treating with 34 g of p-toluenesulphonic acid monohydrate in 100 mL of isopropyl alcohol, filtering and cooling. There was obtained 96.8 g of the toluenesulfonate salt, mp 126°–129° C.

E. The maleate salt was prepared by dissolving 70 g of the free base in 250 mL of isopropyl alcohol and 1 L of isopropyl acetate, adding 20.8 g of maleic acid, refluxing, cooling and stripping. The resulting residue was suspended in about 600 mL of ethyl acetate and 12.8 mL of water was added with vigorous stirring. The resulting solid was filtered off and recrystallized from 300 mL of water to yield 58.9 g of N-[3-(diethylamino)propyl]-4,5-diphenyl-1H-pyrazole-1-acetamide (Z)-2-butenedioate (1:1) sesquihydrate, mp 70°–71° C.

EXAMPLE 13

N-[3-(Dimethylamino)propyl]-4,5-diphenyl-1H-pyrazole-1-acetamide monohydrochloride hemihydrate A mixture of 86.5 g (0.28 mol) of ethyl 4,5-diphenyl-1H-pyrazole-1-acetate of Example 1 and 340 mL (2.8 mol) of dimethylaminopropylamine was stirred on a steam bath under nitrogen for 18 hours. The excess dimethylaminopropylamine was stripped in vacuo, the residue was dissolved in 700 mL of ether and washed two times with water. On washing with saturated sodium chloride solution, the ether layer solidified. The resulting solid was filtered off and dissolved in dichloromethane, washed with saturated sodium chloride solution, and stripped. The residue was slurried in water and the solid product filtered off. After thorough drying, it was dissolved in 700 mL of absolute ethanol, treated with a slight excess of ethanolic HCl, filtered free of some undesired solids, and stripped. The residue was recrystallized from about 800 mL of ethanol by chilling to yield 79 g of the hydrochloride ethanol solvate, mp 101°–104° C., which showed a single spot on TLC on silica gel with 5% isopropyl amine in chloroform as eluant. The ethanol solvate was dissolved in about 800 mL of warm isopropyl alcohol and stripped; the process was repeated and the resulting residue was crystallized from about 350 mL of wet THF by recycling the mother liquor several times to yield 26.2 g of N-[3-(dimethylamino)propyl]-4,5-diphenyl-1H-pyrazole-1-acetamide monohydrochloride hemihydrate, mp 118°–121° C.

EXAMPLE 14

N-[2-(Dimethylamino)ethyl]-4,5-diphenyl-1H-pyrazole-1-acetamide hemihydrate

A mixture of 9 g (0.029 mol) of ethyl 4,5-diphenyl-1H-pyrazole-1-acetate of Example 1 and 31 mL (0.29 mol) of dimethylaminoethylamine was stirred on a steam bath under nitrogen for 18 hours. The excess dimethylamino ethylamine was stripped in vacuo, the residue dissolved in 300 mL of ether, treated with decolorizing carbon, filtered, and stripped to approximately 10 g of residue. This was triturated in water, filtered, washed and recrystallized from ether to yield 7.16 g of N-[2-(dimethylamino)ethyl]-4,5-diphenyl-1H-pyrazole-1-acetamide hemihydrate, mp 85°-88° C.

EXAMPLE 15

N-[6-(Dimethylamino)hexyl]-4,5-diphenyl-1H-pyrazole-1-acetamide

A mixture of 8 g (0.026 mol) of ethyl 4,5-diphenyl-1H-pyrazole-1-acetate of Example 1, 4.1 g (0.028 mol) of dimethylaminohexylamine and 33.3 mL (0.19 mol) of diisopropylethylamine was stirred on a steam bath under nitrogen for 18 hours. Thin layer chromatography on silica gel with 5% isopropylamine in chloroform showed incomplete reaction. Another 1 mL of dimethylaminohexylamine was added and stirring continued on a steam bath for an additional 24 hours. The reaction was stripped in vacuo, taken up in 200 mL of ether, washed two times with water, washed once with half saturated sodium bicarbonate solution, washed with water again, washed with saturated sodium chloride solution, dried over magnesium sulfate, treated with decolorizing carbon, filtered and stripped. The residue was taken up in ether and treated with a slight excess of hydrochloric acid. The hydrochloride salt was extracted into water and washed three times with ether; the water layer was chilled, and made basic with solid sodium carbonate and extracted two times with ether. The ether extracts were combined, washed once with saturated sodium chloride, dried over magnesium sulfate, treated with decolorizing carbon, filtered and stripped. The resulting residue was triturated in pentane to yield 4.14 g of N([6-(dimethylamino)hexyl]-4,5-diphenyl-1H-pyrazole-1-acetamide, mp 60°-63° C.

EXAMPLE 16

N-[4-(Dimethylamino)butyl]-4,5-diphenyl-1H-pyrazole-1-acetamide

By a procedure substantially similar to that of Example 15, 3.91 g of N-[4-(dimethylamino)butyl]-4,5-diphenyl-1H-pyrazole-1-acetamide, mp 77°-79° C., was synthesized from 8 g (0.026 mol) of ethyl 4,5-diphenyl-1H-pyrazole-1-acetate, 3.4 g of dimethylaminobutylamine (0.029 mol) and 3.33 mL (0.18 mol) of diisopropylethylamine.

EXAMPLE 17

N-[2-(Diethylamino)ethyl]-4,5-diphenyl-1H-pyrazole-1-acetamide

By a procedure involving reaction conditions substantially similar to those of Example 14 and a workup substantially similar to that of Example 12, 6.46 g of N-[2-(diethylamino)ethyl]-4,5-diphenyl-1H-pyrazole-1-acetamide, mp 67°-69° C., was synthesized from 10 g of ethyl 4,5-diphenyl-1H-pyrazole-1-acetate and 46.4 mL of N,N-diethylethylenediamine. The product was recrystallized from ether.

EXAMPLE 18

4,5-Diphenyl-N-[2-(1-piperidinyl)ethyl]-1H-pyrazole-1-acetamide

By a procedure substantially similar to that of Example 15, 10.57 g of 4,5-diphenyl-N-[2-(1-piperidinyl)ethyl]-1H-pyrazole-1-acetamide was synthesized from 15 g of ethyl 4,5-diphenyl-1H-pyrazole-1-acetate, 9.2 g of N-(2-aminoethyl)piperidine, and 62 mL of diisopropylethylamine. The work up did not require extraction, as the product crystallized from the cooled reaction mixture. It was recrystallized very slowly from 250 mL of 1:3 THF-ether, mp 95°-97° C.

EXAMPLE 19

4,5-Diphenyl-N-[3-(1-pyrrolidinyl)propyl]-1H-pyrazole-1-acetamide

By a procedure substantially similar to that of Example 14, 5.52 g of 4,5-diphenyl-N-[3-(1-pyrrolidinyl)propyl]-1H-pyrazole-1-acetamide, mp 75°-79° C., was prepared from 15 g of ethyl 4,5-diphenyl-1H-pyrazole-1-acetate and 60 mL of N-(3-aminopropyl)pyrrolidine.

EXAMPLE 20

4,5-Diphenyl-N-[2-(1-pyrrolidinyl)ethyl]-1H-pyrazole-1-acetamide

By a procedure substantially similar to that of Example 18, 6.67 g of 4,5-diphenyl-N-2-(1-pyrrolidinyl)ethyl]1H-pyrazole-1-acetamide, mp 80°-84° C., was prepared from 15 g (0.049 mol) of ethyl 4,5-diphenyl-1H-pyrazole-1-acetate of Example 1, 9 mL (0.072 mol) of N-(2-aminoethyl)pyrrolidine and 62 mL (0.36 mol) of diisopropylethylamine.

EXAMPLE 21

4,5-Diphenyl-N-[3-(1-piperidinyl)propyl]-1H-pyrazole-1-acetamide hemihydrate

A mixture of 15 g (0.049 mol) of ethyl 4,5-diphenyl-1H-pyrazole-1-acetate of Example 1, 10.2 g (0.02 mol) of 3-aminopropylpiperidine, and 62 mL of diisopropylethylamine was stirred on a steam bath under nitrogen for 18 hours. The excess amine was stripped in vacuo. The residue was taken up in about 300 mL of ether and washed twice with water. The product was extracted into 150 mL of cold water containing 18 mL of 10% hydrochloric acid. The water layer was washed two times with ether, treated with decolorizing carbon, filtered, chilled and made basic with solid sodium carbonate. The product was extracted into methylene dichloride, dried over sodium sulfate, filtered, and stripped to 14.7 g of solid residue. The residue was triturated in water, filtered and dried to yield 12.36 g of 4,5-diphenyl-N-[3-(1-piperidinyl)propyl]-1H-pyrazole-1-acetamide hemihydrate, mp 81°-85° C.

EXAMPLE 22

N-[3-(Diethylamino)propyl]-4,5-bis(4-fluorophenyl)-1H-pyrazole-1-acetamide

By a procedure substantially similar to that of Example 14, 8 g (0.023 mol) of ethyl 4,5-bis(4-fluorophenyl)-1H-pyrazole-1-acetate of Example 3 and 34.3 mL (0.22 mol) of diethylaminopropylamine were reacted to produce 4.45 g of N-[3-(diethylamino)propyl]-4-5-bis(4-fluorophenyl)-1H-pyrazole-1-acetamide. The solid product after trituration in water collapsed to a non-crystalline, white, waxy solid upon drying.

EXAMPLE 23

N-[3-(Diethylamino)propyl]-N-methyl-4,5-diphenyl-1H-pyrazole-1-acetamide (E)-2-butenedioate (1:1)

A mixture of 28.7 g (0.09 mol) of ethyl 4,5-diphenyl-1H-pyrazole-1-acetate of Example 1, 19.7 g (0.13 mol) of diethylaminopropylmethylamine, and 94 mL (0.54 mol) of diisopropylethylamine was refluxed under nitrogen for seven days. The reaction was stripped and applied to a silica gel column using dichloromethane.

Impurities were eluted with dichloromethane followed by 1.25% isopropylamine in dichloromethane. The product was eluated with 1.25% isopropylamine in chloroform. The 8 g of product was dissolved in 40 mL of warm acetone and treated with 2.3 g of fumaric acid. Upon cooling, there was obtained 9.87 g of N-[3-(diethylamino)propyl]-N-methyl-4,5-diphenyl-1H-pyrazole-1-acetamide(E)-2-butenedioate (1:1), mp 139°-141° C.

EXAMPLE 24

N-[3-[bis(1-methylethyl)amino]propyl]-4,5-diphenyl-1H-pyrazole-1-acetamide

By a procedure substantially similar to that of Example 15, 2.49 g of N-[3-[bis(1-methylethyl)amino]propyl]-4,5-diphenyl-1H-pyrazole-1-acetamide, mp 83°-84° C., was synthesized from 12 g (0.039 mol) of ethyl 4,5-diphenyl-1H-pyrazole-1-acetate, 6.2 g (0.039 mol) of diisopropylaminopropylamine, and 35 mL of diisopropylethylamine.

EXAMPLE 25

N-[3-(Diethylamino)-2-hydroxypropyl]-4,5-diphenyl-1H-pyrazole-1-acetamide

By a procedure substantially similar to that of Example 15, 8.9 g of N-[3-(diethylamino)-2-hydroxypropyl]-4,5-diphenyl-1H-pyrazole-1acetamide, mp 70°-72° C., was synthesized from 15 g (0.049 mol) of ethyl 4,5-diphenyl-1H-pyrazole-1-acetate, 10 g (0.69 mol) of 1-amino-3-diethylamino-2-propanol, and 57 mL of diisopropylethylamine.

EXAMPLE 26

N-[3-(Dimethylamino)propyl]-3,4-diphenyl-1H-pyrazole-1-acetamide (E)-2-butenedioate (1:1)

A mixture of 8.35 g (0.027 mol) of ethyl 3,4-diphenyl-1H-pyrazole-1-acetate of Example 2 and 33.4 mL (0.26 mol) of dimethylaminopropylamine was stirred on a steam bath under nitrogen for 18 hours. The reaction was stripped to dryness, the residue dissolved in dichloromethane, washed twice with water and once with saturated sodium chloride solution. The product was extracted into about 100 mL of cold water containing about 12 mL of 10% HCl. The water layer was made basic with solid sodium carbonate and the product extracted into methylene dichloride, dried over sodium sulfate and stripped. The product was purified by chromatography on silica gel eluting with 5% triethylamine in chloroform. The purified product was crystallized from acetone as the fumarate salt and was recrystallized from ethanol to yield 4.47 g of N-[3-(dimethylamino)propyl]-3,4-diphenyl-1H-pyrazole-1-acetamide (E)-2-butenedioate (1:1), mp 163°-168° C.

EXAMPLE 27

N-[3-(Diethylamino)propyl]-3,4-diphenyl-1H-pyrazole-1-acetamide

By a procedure substantially similar to that of Example 26, omitting the formation of the fumarate salt, 9 g of N-[3(diethylamino)propyl]-3,4-diphenyl-1H-pyrazole-1-acetamide was prepared from 10 g (0.033 mol) of ethyl 3,4-diphenyl-1H-pyrazole-1-acetate and 50 mL (0.32 mol) of diethylaminopropylamine. The product was an oil.

EXAMPLE 28

3,4-Diphenyl-N-[2-(1piperidinyl)ethyl-]1H-pyrazole-1-acetamide

By a procedure substantially similar to that of Example 18, 14.0 g of 3,4-diphenyl-N-[2-(1piperidinyl)ethyl]1H-pyrazole-1-acetamide was prepared from 16.4 g (0.054 mol) of ethyl 3,4-diphenyl-1H-pyrazole-1-acetate, 10 g (0.07 mol) of 2-aminoethylpiperidine, and 65 mL (0.37 mol) of diisopropylethylamine. The product was not recrystallized but was triturated in ether, mp 120°-124° C. A second polymorph of mp 142°-144° C. may be obtained by recrystallizing from ecetate.

EXAMPLE 29

3,4-Diphenyl-N-(1-piperidinyl)propyl]-1H-pyrazole-1-acetamide (E)-2-butenedioate (1:1)

By a procedure substantially similar to that of Example 26, 8.56 g of 3,4-diphenyl-N-[3-(piperidinyl)propyl]-1H-pyrazole-1-acetamide (E)-2-butanedioate (1:1), mp 179°-180° C., was prepared from 20 g (0.065 mol) of ethyl 3,4-diphenyl-1H-pyrazole-1-acetate, 13.7 g (0.096 mol) of 3-aminopropylpiperidine, and 78 mL (0.45 mol) of diisopropylethylamine.

EXAMPLE 30

N-[2-(Diethylamino)ethyl]-3,4-diphenyl-1H-pyrazole-1-acetamide

A mixture of 10 g (0.033 mol) of ethyl 3,4-diphenyl-1H-pyrazole-1-acetate, 6.9 mL (0.049 mol) of diethylaminoethylamine and 39 mL of diisopropylethylamine was stirred on a steam bath under nitrogen for 18 hours. The reaction was stripped, the residue taken up in about 300 mL of ether and washed twice with water. The ether layer was extracted twice with a total of 150 mL of cold water containing 20 mL of 10% HCl. The combined water extracts were washed once with ether, colled, made basic with solid sodium carbonate, extracted several times with methylene dichloride, dried over sodium sulphate, treated with decolorizing carbon, filtered and stripped. The oily red residue was crystallized from ether to yield 6.86 g of N-[2-diethylamino)ethyl]-3,4-diphenyl-1H-pyrazole-1-acetamide, mp 80°-83° C.

EXAMPLE 31

N-(3-Aminopropyl)-4,5-diphenyl-1H-pyrazole-1-acetamide (1:4) hydrate

A mixture of 7.96 g (0.026 mol) of ethyl 3,4-diphenyl-1H-pyrazole-1-acetate and 19.2 g (0.26 mol) of 1,3-diaminopropane in 13 mL of ethanol was stirred at 84°-87° C. for 3 hours and the solvent removed in vacuo. The resulting solid was chromatographed on 34 g of silica gel eluting with 1% isopropylamine in chloroform and a gradient from 0-30% methanol. The impurities came off at 2-4% methanol followed by 6.95 g of pure product. It was crystallized three times from isopropyl acetate to yield 6.09 g of N-(3-aminopropyl)-4,5-diphenyl-1H-pyrazole-1-acetamide (1:4) hydrate, mp 119°-120° C.

EXAMPLE 32

N-(3-Hydroxypropyl)-4,5-diphenyl-1H-pyrazole-1-acetamide

A mixture of 1.47 g (0.0048 mol) of ethyl 4,5-diphenyl-1H-pyrazole-1-acetate of Example 1, 0.72 g (0.0096 mol) of 3-amino-1-propanol and 0.024 g (0.00024 mol) of triethylamine was stirred at 100° C. for two hours. Five mL of ethanol was added and the solution was poured into 20 mL of water and allowed to stand 18 hours at 5° C. to crystallize. The product was filtered off, air-dried and recrystallized from 25 mL of ethyl acetate to yield 1.47 g of N-(3-hydroxypropyl)-4,5-diphenyl-1H-pyrazole-1-acetamide, mp 138°–139° C.

EXAMPLE 33

N-[3[(2-Hydroxyethyl)amino]propyl]-4,5-diphenyl-1H-pyrazole-1-acetamide hydrochloride A solution of 83 6 g of N-(3-hydroxypropyl)-4,5-diphenyl-1H-pyrazole-1acetamide of Example 32 in 250 mL of pyridine was cooled to −11° C. and 29 mL (0.375 mL) of methanesulfonyl chloride was added in 5 mL of aliquots.

The reaction temperature was maintained below 0° throughout the addition and for ½ hour after the completion of the addition. The resulting mixture was poured into 2 kg of ice and 2 L of 1M HCl, stirred vigorously for ½ hour, and then allowed to stand until the ice melted. The water was decanted and the oil dissolved in 1 L of dichloromethane. The dichloromethane solution was dried with magnesium sulfate, filtered and stripped. Forty-five g of the resulting oil, which contained approximately 34 g (0.083 mol) of the methanesulfonate, was mixed with 25.4 mL (0.026 mol) of ethanolamine, heated briefly to avoid crystallization and then stirred overnight at room temperature. Three hundred mL of saturated aqueous sodium bicarbonate was added and the product extracted into dichloromethane. The dichloromethane was separated, dried over magnesium sulfate and chromatographed on 1.1 kg of alumina using a gradient of 0–100% methanol in dichloromethane followed by step gradients of 1% and 2% isopropylamine in methanol and finally chloroform/methanol/isopropylamine, 50:45:5. The product came off from 75% methanol in dichloromethane through to the column wash with chloroform/methanol/isopropylamine. It was then chromatographed on silica gel using a gradient of 0–30% methanol and chloroform followed by a gradient of 0.012% to 2% isopropylamine in dichloromethane/methanol, 70:30. The pure product came off from 18% methanol in dichloromethane through to the 2% isopropylamine in dichloromethane/methanol 70:30. The resulting 13.3 g of residue was recrystallized twice from ethanol to yield 6.16 g of N-[3[(2-hydroxyethyl)amino]propyl]-4,5-diphenyl-1H-pyrazole-1-acetamide hydrochloride, mp 161°–163° C.

EXAMPLE 34

N-[3-[Ethyl(2-hydroxyethyl)amino]propyl]-4,5-diphenyl-1H-pyrazoleacetamide (E)-2-butenedioate (1:1)

Forty-five g of the impure methanesulfonate intermediate of Example 33 was stirred at room temperature for 18 hours with 41 mL (0.037 mol) of 2-(ethylamino)ethanol in 130 mL of ethanol. The mixture was filtered, 300 mL of saturated aqueous sodium bicarbonate was added, and the product extracted into dichloromethane. The residue after removal of the methylene dichloride was chromatographed substantially in the same manner as Example 26. The resulting amorphous solid was dissolved in 50 mL of isopropanol and 3 g of fumaric acid was added; the resulting solid was dried and lixiviated in refluxing acetonitrile to yield 10.1 g of N-[3-[ethyl(2-hydroxyethyl)aminopropyl]4,5-diphenyl-1H-pyrazoleacetamide(E)-2-butanedioate (1:1), mp 157°–158° C.

EXAMPLE 35

4,5-Diphenyl-N-[3-(ethylamino)propyl]-1H-pyrazole-1-acetamide hydrochloride

A. A solution of 10 g (0.03 mol) of 4,5-diphenyl N-(3-hydroxypropyl)-1H-pyrazole-1-acetamide of Example 32 in 50 mL of pyridine was stirred at 0°–5° C. and 5.2 mL (0.066 mol) of methanesulfonyl chloride was added dropwise over 30 minutes. The reaction was filtered free of pyridine hydrochloride and added dropwise rapidly to 40 mL of ethylamine in 50 mL of pyridine at 0°–5° C. The reaction was heated 30 minutes on a steam bath, stripped in vacuo, dissolved in 100 mL of water, washed once with ethyl acetate, made strongly basic with aqueous KOH, extracted into ethyl acetate, dried and stripped to 9.9 g of free base which was a yellow oil. The oil was treated with 75 mL of 5N HCl in ethanol and 5 g of product was filtered off. The mother liquor was treated with about 75 mL of ether and a second crop of product obtained. The total yield of 4,5-diphenyl-N-[3-(ethylamino)propyl]-1H-pyrazole-1-acetamide hydrochloride was 6.5 g, m.p. 135°–137° C.

B. The dihydrochloride sat was prepared by dissolving 12 parts of the free base in 12 parts of ethanol, adding 2 equivalents (about 12 parts by volume) of 5N HCl in ethanol, 1 part of water and 5 parts of ether. The resulting solid was filtered and recrystallized from isopropyl alcohol to yield 58% of the dihydrochloride salt, mp 166°–174° C.

C. The fumarate salt was prepared by dissolving part of the free base in 6 parts of isopropyl alcohol, adding one equivalent of fumaric acid, heating to complete solution, cooling and filtered off the fumarate monohydrate, mp 127°–129° C. in 86% yield.

EXAMPLE 36

N-[3-(Diethylamino)propyl]-4,5-diphenyl-1H-pyrazole-1-propanamide hemihydrate

A solution of 4.8 g (0.016 mol) of methyl 4,5-diphenyl-1H-pyrazole-1-propanoate of example 4 and 48 mL of diethylaminopropylamine was heated at 120°–125° C. under nitrogen for 14 hours. The excess diethylaminopropylamine was stripped in vacuo at 85° C. The residue was dissolved in dichloromethane, an unwanted solid residue was filtered off, and the methylene chloride solution was washed twice with water and once with brine. The product was extracted into chilled dilute hydrochloric acid, and the chilled aqueous acid was made basic with solid sodium bicarbonate and then sodium carbonate. The basic water was extracted 4 times with dichloromethane, the combined washings were dried over sodium sulfate, and stripped to yield 2.4 g viscous amber oil. The oily product was dried at 40° C. and 0.1 mm vacuum for 7 days to yield 1.6 g of the hemihydrate still as a viscous oil.

EXAMPLE 37

N-[3-(Diethylamino)ethyl]-4,5,-diphenyl-1H-pyrazole-1-propanamide

By a procedure substantially similar to that of example 36, except that the temperature was maintained at 105° C., 1.1 g of N-[3-(diethylamino)ethyl]-4,5-diphenyl-1H-pyrazole-1-propanamide, mp 83°–84° C., was synthesized from 1.8 g (5.9 mmol) of methyl 4,5-diphenyl pyrazole propanoate of example 4 and 8.3 mL (59 mmol) of diethylaminoethylamine. The product was recrystallized from 125 mL of cyclohexane containing 0.04 mL of water.

EXAMPLE 38

N-[3-(Diethylamino)propyl]-4-(4-methoxyphenyl)-5-phenyl-1H-pyrazole-1-acetamide

A solution of 7.5 g (0.022 mol) of ethyl 4-(4-methoxyphenyl)-5-phenyl-1H-pyrazole-1-acetate of example 5 in 35 mL of diethylaminopropylamine was stirred on a steam bath under nitrogen for 14 hours. The diethylaminopropylamine was removed in vacuo and the residue taken up in 200 mL of ethyl acetate. The ethyl acetate solution was washed twice with water, once with brine, and dried over sodium sulfate. The solvent was removed in vacuo and the residue was distilled in a Kugelrohr at 250° C./0.1 mm to yield 6.39 g of N-[3-(diethylamino)propyl]-4-(4-methoxyphenyl)-5-phenyl-1H-pyrazole-1-acetamide as a clear viscous amber oil.

EXAMPLE 39

N-[3-(Diethylamino)propyl]-4-(4-hydroxyphenyl)-5-phenyl-1H-pyrazole-1-acetamide

A solution of 14 g (00.33 mol) of N-[3-(diethylamino)propyl]-4-(4-methoxyphenyl)-5-phenyl-1H-pyrazole-1-acetamide of example 38 and 0.16 mol of the sodium salt of 1-propanethiol in 375 mL of DMF was heated at 155°–160° C. for 2 hours. The reaction was chilled and the excess thiopropoxide was neutralized with ethanolic HCl. The DMF solution was stripped under vacuum at 30°, dissolved in methylene dichloride, and washed with aqueous sodium carbonate, the water, and finally brine. The methylene chloride was dried over sodium sulfate and the solvent removed in vacuo to yield 13.4 g of gummy product. Seven grams of the gummy product was chromatographed on a silica gel column eluted with methanol/isopropylamine/chloroform (2:3:95) to yield 5.1 g of purified product. The residue was taken up in isopropyl acetate, washed twice with water, washed once with brine, and dried over sodium sulfate. The isopropyl acetate was evaporated in vacuo, but removal of the last traces of isopropyl acetate required extensive drying under vacuum to yield 2.5 g of product as a glass.

EXAMPLE 40

N-[3-(diethylamino)propyl]-5-(4-hydroxyphenyl)-4-phenyl-1H-pyrazole-1-acetamide.

A solution of 10 g (0.031 mol) of ethyl-5-(4-hydroxyphenyl)-4-phenyl-1H-pyrazole-1-acetate of example 6 in 48 mL of diethylaminopropylamine was stirred on a steam bath under nitrogen for 14 hours. The excess amine was removed in vacuo at 80° C., the residue dissolved in ethyl acetate, washed twice with water, once with brine and dried over sodium sulfate. The ethyl acetate was stripped to yield 12 g of a dark oil which was triturated in hot cyclohexane several times. The insoluble residue was combined with a small amount of a mixture of oil and crystals, which had separated from the cyclohexane on cooling, and recrystallized from ethyl acetate to yield 6.6 g of product, mp 110–113.

EXAMPLE 41

4,5-Diphenyl-N-[3-(2-methyl-1-piperidinyl)propyl]-1H-pyrazole-1-acetamide hemihydrate A solution of 15 g (0.049 mol) of ethyl 4,5-diphenyl-1H-pyrazole-1-acetate of example 1 in 17 mL (0.098 mol) of 1-(3-aminopropyl)-2-pipecoline was stirred on a steam bath for five hours. The solution was distributed between ether and water, the layers separated, and the ether layer washed several times with water. The ether solution was dried over magnesium sulfate and stripped to about 20 g of yellow oil. The oil was triturated in cyclohexane with a seed crystal obtained from the aqueous layer upon standing. The resulting white solid was filtered off and rinsed with cyclohexane to yield 17.0 g of the hemihydrate, mp 75°–76° C.

EXAMPLE 42

N-[2-[(1,1-dimethylethyl)amino]ethyl]-4,5-diphenyl-1H-pyrazole-1-acetamide

A solution of 10.7 g (0.035 mol) of ethyl 4,5-diphenyl-pyrazole-1-acetate of example 1 in 10.9 g (0.094 mol) of 2-[(1,1-dimethylethyl)amino]ethanamine was heated with about 50 mg of sodium methoxide at about 150° for two hours. The excess amine was stripped off under vacuum and the residue was triturated in acetonitrile. The solid product was filtered off and recrystallized from isopropyl acetate to yield 8.8 g of white crystals, mp 115°–116° C.

EXAMPLE 43

N-[3-[(1,1-dimethylethyl)amino]propyl]-4,5-diphenyl-1H-pyrazole 1-acetamide (E)-2-butenedioate (1:1)

A solution of 9.18 g (0.03 mol) of ethyl 4,5-diphenyl-pyrazole-1-acetate of example 1 in 13.8 g (0.106 mol) of 3-[(1,1-dimethylethyl)amino]propanamine was heated to about 100° C., the lower boiling material was allowed to boil off, and the temperature was raised to 180° C. for one hour. The solution was cooled to 95° and the excess amine was removed by vacuum distillation. The residual oil was dissolved in 100 mL of acetone and treated with 3.48 g of fumaric acid. The acetone was stripped, the residue dissolved in methanol, and isopropyl alcohol was added. The solution was boiled down until the product crystallized. It was recrystallized from ethanol/acetonitrile to yield 4.88 g, mp 234°–235° C.

EXAMPLE 44

N-[3-(Diethylamino)propyl]-4-(4-fluorophenyl)-5-phenyl-1H-pyrazole-1-acetamide

A solution of 8.73 g (0.027 mol) of ethyl 4-(4-fluorophenyl)-5-phenyl-1H-pyrazole-1-acetate of example 7 in 30 mL of 3-(diethylamino)propanamine was heated at reflux for 3 hr. The excess amine was stripped under vacuum and the residue triturated in 1:1 hexane/methyl t-butyl ether. The solid was recrystallized from triethylamine to yield 8.4 g of product, mp 82°–83° C.

EXAMPLE 45

N-[3-(Diethylamino)propyl]-4-(4-nitrophenyl)-5-phenyl-1H-pyrazole-1-acetamide

A solution of 3.51 g (0.01 mol) of ethyl 4-(4-nitrophenyl)-5-phenyl-1H-pyrazole-1-acetate of example 8 in 10 mL of 3(diethylamino)propanamine was reacted as in example 44. The product was recrystallized from methyl t-butyl ether to yield 5.4 g, mp 100°–101° C.

EXAMPLE 46

4-(4-Aminophenyl)-N-[3-(diethylamino)propyl]-5-phenyl-1H-pyrazole-1-acetamide

A solution of 43.7 g (0.1 mol) of N-[3-(diethylamino)propyl]-4-(4-nitrophenyl)-5-phenyl-1H-pyrazole-1-acetamide of example 45 in 200 mL of methanol was refluxed for 2 hr with 4 g of 10% palladium on charcoal and 30 g of ammonium formate. The catalyst was filtered off and the filtrate was stripped. The residue was distributed between aqueous NaOH and 1:1 THF-ether. The ether layer was dried over magnesium sulfate, stripped and recrystallized from methyl t-butyl ether to yield 38.9 g of product, mp 75°–76° C.

EXAMPLE 47

4-(4-Acetylaminophenyl)-N-[3-diethylamino)propyl]-5-phenyl-1H-pyrazole-1-acetamide A solution of 1.3 g (3.2 mmol) of 4-(4-aminophenyl)-N-[3-(diethylamino)propyl]-5-phenyl-1H-pyrazole-1-acetamide of example 46 in 10 mL of acetic anhydride was heated at 100° for 30 min., allowed to sit at room temperature for 3 hours, diluted with 20 mL of methanol, and concentrated in vacuo. The product was recrystallized twice from acetonitrile, mp 150°–151° C.

EXAMPLE 48

N-[3-(Diethylamino)propyl]-4-[4-(methylsulfonylamino)phenyl]-5-phenyl-1H-pyrazole-1-acetamide A solution of 8 1g (0.02 mol) of 4-(4-aminophenyl)-N-[3-(diethylamino)propyl]-5-phenyl-1H-pyrazole-1-acetamide of example 46 in 50 mL of pyridine was cooled to 5° C. and 4.6 g (0.04 mol) of methanesulfonyl chloride was added dropwise below 10° C. The reaction was stripped below 60° C. in vacuo, dissolved in about 75 mL of water, treated with excess saturated aqueous sodium bicarbonate, extracted into methylene chloride and stripped. The product was recrystallized from acetonitrile, 7.2 g, mp 179°–180° C.

EXAMPLE 49

4-(4-Chlorophenyl)-N-[3-diethylamino)propyl]-5-phenyl-1H-pyrazole-1-acetamide

By a process analogous to that of example 44, 7.35 g of 4-(4-chlorophenyl)-N-[3-(diethylamino)propyl]-5-phenyl-1H-pyrazole-1-acetamide, mp 104°–105° C. from triethylamine, was synthesized from 6.8 g (0.02 mol) of ethyl 4-(4-chlorophenyl)-5-phenyl-1H-pyrazole-1-acetate of example 9 and 25 mL of 3-(diethylamino)propanamine.

EXAMPLE 50

4-(4-Cyanophenyl)-N-[3-(diethylamino)propyl]-5-phenyl-1H-pyrazole-1-acetamide

By a process analogous to that of example 44, 6.5 g of 4-(4-cyanophenyl)-N-[3-(diethylamino)propyl]-5-phenyl-1H-pyrazole-1-acetamide, mp 100°–101° C. from triethylamine, was synthesized from 6.7 g (0.02 mol) of ethyl 4-(4-cyanophenyl)-5-phenyl-1H-pyrazole-1-acetate of example 10 and 25 mL of 3-(diethylamino)propanamine.

EXAMPLE 51

N-[3-(Diethylamino)propyl]-5-4-(dimethylamino)phenyl]4-phenyl-1H-pyrazole-1-acetamide A solution of 9 g (0.026 mol) of ethyl 5-[4-(dimethylamino)phenyl]-4-phenyl-1H-pyrazole-1-acetate of example 11 and 30 mL of 3-(diethylamino) propanamine was refluxed for 6 hr. The excess amine was stripped under vacuum and the residue was crystallized from ether to yield 4.4 g of product, mp 66°–68° C.

EXAMPLE 52

N-[3-(Diethylamino)propyl]-4-(4-hydroxy-3-methoxyphenyl)-5-phenyl-1H-pyrazole-1-acetamide By a process substantially similar to that of example 40 it is contemplated that N-[3-(diethylamino)propyl]-4-(4-hydroxy-3-methoxyphenyl)-5-phenyl-1H-pyrazole-1-acetamide may be synthesized from 3-(diethylamino)propanamine and ethyl 4-(4-hydroxy-3-methoxyphenyl)-5-phenyl-1H-pyrazole-1-acetate, which may be synthesized by a process substantially similar to that of example 1B from 1-(4-hydroxy-3-methoxyphenyl)-2-phenylethanone and ethyl hydrazinoacetate hydrochloride.

EXAMPLE 53

4-(4-Bromophenyl)-N-[4-(ethylmethylamino)butyl]-5-phenyl-1H-pyrazole-1-acetamide By a process substantially similar to that of Example 30 it is contemplated that 4-(4-bromophenyl)-N-[4-(ethylmethylamino)butyl]5-phenyl-1H-pyrazole-1-acetamide may be synthesized from N-ethyl-N-methyl-1,4-butanediamine and ethyl 4-(4-bromophenyl)-5-phenyl-1H-pyrazole-1-acetate, which is synthesized by a process substantially similar to that of Example 1A from α-(4-bromophenyl)-62-oxobenzenepropanal.

EXAMPLE 54

4-(2-Chlorophenyl)-N-[3-[(1,1-dimethylethyl)amino]propyl]-5-(4-methoxyphenyl)-1H-pyrazole-1-acetamide By a process substantially similar to that of Example 35 it is contemplated that 4-(2-chlorophenyl)-N-[3-[(1,1-dimethylethyl)amino]propyl]-5-(4-methoxyphenyl)-1H-pyrazole-1-acetamide may be synthesized from tert-butylamine and N-[3-(methylsulfonyloxy)propyl]-4(2-chlorophenyl)-5(4-methoxyphenyl)-1H-pyrazole-1-acetamide.

EXAMPLE 55

N-[7-(Diethylamino)heptyl]-4-(3-methylphenyl)-5-phenyl-1H-pyrazole-1-acetamide

By a process substantially similar to that of Example 30 it is contemplated that N-7-(diethylamino)heptyl]-4-(3-methylphenyl)-5-phenyl-1H-pyrazole-1-acetamide may be synthesized from N,N-diethyl-1,7-heptanediamine and ethyl 4-(3-methylphenyl)-5-phenyl-1H-pyrazole-1-acetate, which is synthesized by a process substantially similar to that of Example 1B from 2-(3-methylphenyl)-1-phenylethanone.

EXAMPLE 56

Ethyl 3-hydroxy-4,5-diphenyl-1H-pyrazole-1-acetate or Ethyl 1,2-dihydro-3-oxo-4,5-diphenyl-3H-pyrazol-1-acetate A suspension of 3.3 mL (0.03 mol) of ethyl bromoacetate, 3.9 g (0.028 mol) of anhydrous, milled potassium carbonate and 6.7 g (0.028 mol) of 1,2-dihydro-4,5-diphenyl-3H-pyrazol-3-one obtained by the method of Gruenanger and Finzi [Chemical Abstracts 58: 516 f (1963)] in 67 mL of acetone was stirred at reflux for 24 hours. The solvent was removed in vacuo and the residue was chromatographed on a 45×300 mm silica gel column eluting with a gradient from 0 to 10% ethyl acetate in hexane, taking 75 mL fractions. Fractions 50-65 contained the O-alkylated product; fractions 75-79 provided 1.1 g of the desired N-alkylated product, mp 181°-183° C.

EXAMPLE 57

N-[3-(Diethylamino)propyl]-3-hydroxy-4,5-diphenyl-1H-pyrazole-1-acetamide or N[3-(Diethylamino)propyl]-1,2-dihydro-3-oxo-4,5-diphenyl-3H-pyrazole-1-acetamide hemihydrate By a process substantially similar to that of example 40, 400 mg of N-[3-(diethylamino)propyl]-3-hydroxy-4,5-diphenyl-1H-pyrazole-1-acetamide or N[3-(diethylamino)propyl]-1,2-dihydro-3-oxo-4,5-diphenyl-3H-pyrazole-1-acetamide was prepared from 1.1 g (3.4 mmol) of ethyl 3-hydroxy-4,5-diphenyl-1H-pyrazole-1-acetate of example 56 and 5.1 mL (32 mmol) of diethylaminopropyl amine. The oily product was triturated in ether and the resulting crystals filtered off and dried. The product from ether was slurried in water and filtered to yield the hemihydrate, mp 150°-152° C.

The antiarrhythmic activity of compounds of the invention was demonstrated by the following procedure.

Duncan Hartley guinea pigs (600-900 grams) of either sex were anesthetized with urethane (1.4 g/kg, i.p.) and supplemented as needed. An intravenous route for drug administration was established using microbore tubing inserted into the jugular vein. The induction of arrhythmias by aconitine hydrochloride (34 mg/kg) was evaluated in control guinea pigs given 1 mL saline as an intravenous bolus 10 minutes prior to aconitine challenge.

Compounds to be tested were administered intravenously 10 minutes prior to aconitine challenge at an initial dosage of 30 mg/kg. This dosage was reduced in subsequent animals if severe cardiac rhythm disturbances persisted beyond two minutes after injection in the first guinea pig tested. All drugs were tested at the maximally tolerated dose (identified by the lack of arrhythmias in the EKG prior to aconitine challenge). Compounds were administered in saline as 1 mL bolus injections (n=5-9).

Time intervals between aconitine injection and the appearance of arrhythmias were determined. Specifically noted was the time until the onset of (i) the first premature ventricular contraction (PVC); (ii) the first sustained run of ventricular tachycardia consisting of 10 or more ventricular beats (VTAH); and (iii) the time until the appearance of ventricular fibrillation lasting longer than 15 seconds (VFIB). The average time and standard error of the mean until the appearance of these arrhythmias were calculated for each treatment group and compared to concurrent controls using a one-way analysis of variance. Activity was defined as a statistically significant delay in the onset of PVC, VTACH and VFIB time course compared to control values.

The following table summarizes the results obtained from the testing of representative compounds of the invention.

| Example No. | Minutes to | | |
|---|---|---|---|
| | PVC | VTACH | VFIB |
| Control | 0.97 | 1.48 | 3.96 |
| 12A | 15.7 | 16.0 | 37.1 |
| 12B | 2.8 | 10.5 | 21.1 |
| 12C | 2.8 | 3.4 | 21.8 |
| 12D | 2.4 | 2.8 | 13.2 |
| 12E | 4.9 | 7.4 | 19.8 |
| 13 | 5.9 | 7.3 | 16.2 |
| 14 | 8.2 | 8.7 | 29.0 |
| 15 | 2.6 | 3.0 | 11.7 |
| 16 | 5.0 | 5.7 | 25.7 |
| 17 | 4.1 | 5.8 | 40.1 |
| 18 | 7.9 | 10.7 | 35.4 |
| 19 | 5.1 | 6.3 | 25.7 |
| 20 | 2.9 | 3.0 | 15.5 |
| 21 | 5.2 | 15.4 | 27.6 |
| 22 | 1.0* | 2.6 | 30.0 |
| 23 | 8.4 | 11.3 | 32.0 |
| 24 | 4.5 | 6.0 | 16.5 |
| 25 | 8.4 | 10.1 | 40.7 |
| 26 | 3.9 | 5.4 | 14.5 |
| 27 | 3.9 | 20.3 | 26.5 |
| 28 | 3.6 | 9.6 | 30.0 |
| 29 | 3.6 | 8.0 | 29.0 |
| 30 | 1.9 | 2.1* | 17.7 |
| 31 | 2.1 | 2.9 | 16.7* |
| 33 | 2.1 | 11.0 | 44.1 |
| 34 | 2.9* | 5.0 | 21.0 |
| 35A | 3.9 | 13.2 | 47.7 |
| 35B | 9.0 | 10.5 | 13.8 |
| 35C | 16.3 | 22.4 | 37.0 |
| 36 | 11.6 | 21.8 | 54.7 |
| 37 | 2.5 | 2.8 | 38.6 |
| 38 | 10.9 | 15.4 | 41.5 |
| 39 | 11.6 | 38.9 | 60.0 |
| 40 | 9.4 | 38.4 | 60.0 |
| 41 | 25.9 | 50.5 | 60.0 |
| 42 | 9.2 | 13.6 | 38.7 |
| 43 | 12.6 | 15.1 | 26.2 |
| 44 | 34.2 | 55.7 | 59.4 |
| 45 | 23.1 | 50.4 | 60.0 |
| 46 | 18.2 | 40.0 | 48.6 |
| 47 | 5.6 | 11.4 | 45.6 |
| 48 | 6.0 | 7.1 | 35.1 |
| 49 | 8.8 | 30.2 | 31.4 |
| 50 | 10.6 | 31.2 | 38.8 |
| 51 | 49.6 | 51.5 | 56.6 |
| 57 | 3.0 | 6.9 | 39.0 |

*not statistically significant

The compounds of the invention can be prepared for use by conventional pharmaceutical procedures: that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf.

I claim:

1. A compound of formula

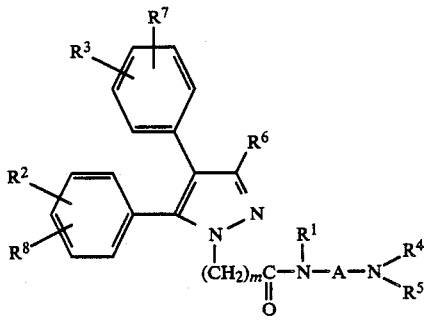

OR

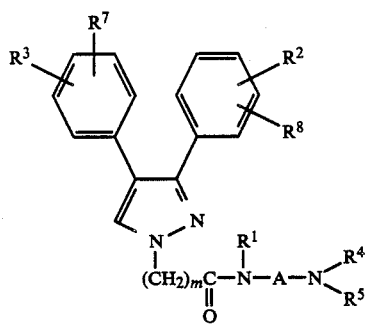

or acid-addition salt thereof wherein $R^1$ is hydrogen or lower-alkyl; $R^2$ and $R^3$ are independently hydrogen, hydroxy, lower-alkyl, lower-alkoxy, lower-alkylamino, lower-alkylamido, lower-alkylsufonamido, nitro, amino, cyano, or halo; $R^4$ and $R^5$ are independently hydrogen, lower-alkyl or hydroxy lower-alkyl, or $R^4$ and $R^5$ together form a straight or branched alkylene chain of four to six carbons; $R^6$ is hydrogen or hydroxy; $R^7$ and $R^8$ are independently hydrogen, hydroxy, lower-alkyl, lower-alkoxy, or halo; m is one or two; and A is $CH_2CH(OH)CH_2$ or $(CH_2)_n$ wherein n is an integer from two to eight.

2. A compound according to claim 1 wherein $R^7$ and $R^8$ are hydrogen.

3. A compound according to claim 2 wherein m is one and having the formula

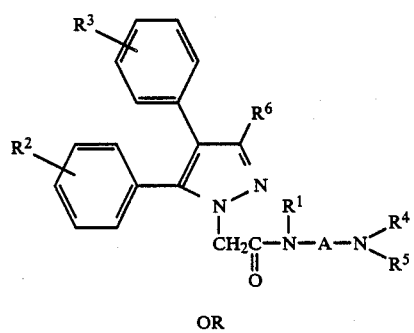

OR

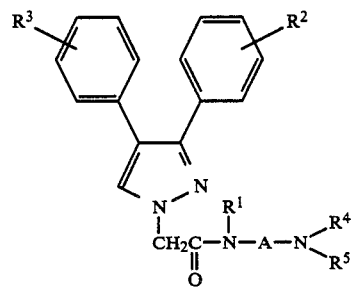

4. A compound according to claim 2 wherein A is $CH_2CH(OH)CH_2$.

5. N-[3-(diethylamino)-2-hydroxypropyl]-4,5-diphenyl-1H-pyrazole-1-acetamide or acid-addition salt thereof according to claim 4.

6. A compound according to claim 2 wherein A is $(CH_2)_n$.

7. A compound according to claim 3 wherein $R^6$ is hydrogen.

8. A compound according to claim 3 wherein A is $(CH_2)_n$.

9. A compound according to claim 8 having the formula.

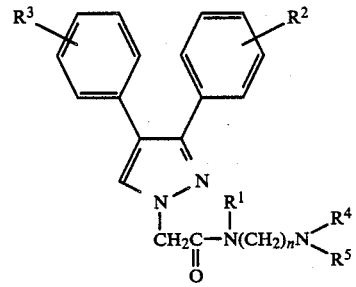

10. A compound according to claim 8 having the formula

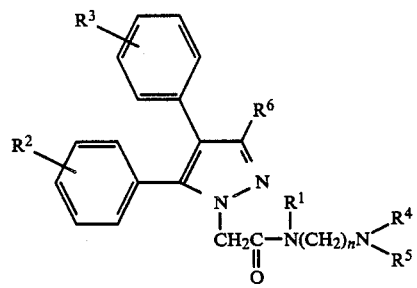

11. A compound according to claim 10 wherein $R^6$ is hydrogen.

12. N-[3-(Diethylamino)propyl]-4,5-diphenyl-1H-pyrazole-1-acetamide or acid-addition salt thereof according to claim 11.

13. N-[3-(Diethylamino)propyl]-bis(4-fluorophenyl)-1H-pyrazole-1-acetamide or acid-addition salt thereof according to claim 11.

14. N-[3-[Bis(1-methylethyl)amino]propyl]-4,5-diphenyl-1H-pyrazole-1-acetamide or acid-addition salt thereof according to claim 11.

15. N-[3-(Ethylamino)propyl]-4,5-diphenyl-1H-pyrazole-1-acetamide according to claim 11.

16. N-[3-(Diethylamino)propyl]-4-(4-hydroxyphenyl)-5-phenyl-1H-pyrazole-1-acetamide according to claim 11.

17. N-[3-(Diethylamino)propyl]-5-(4-hydroxyphenyl)-4-phenyl-1H-pyrazole-1-acetamide according to claim 11.

18. N-[3-(Diethylamino)propyl]-4-(4-methoxyphenyl)-5-phenyl-1-H-pyrazole-1-acetamide according to claim 11.

19. A compound according to claim 2 wherein m is two and having the formula

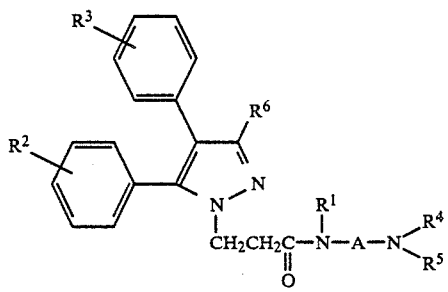

OR

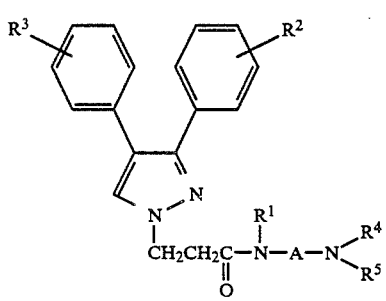

20. A compound according to claim 19 wherein A is $(CH_2)_n$.

21. A compound according to claim 1 wherein m is one.

22. A compound according to claim 21 wherein $R^6$ is hydrogen.

23. A compound according to claim 22 wherein $R^2$, $R^3$, $R^7$, and $R^8$ are independently hydrogen, hydroxy, or methoxy.

24. A composition for treating cardiac arrhythmias comprising an amount of a compound according to claim 1 effective to treat cardiac arrhythmias together with one or more pharmaceutically acceptable excipients or diluents.

25. A composition for treating cardiac arrhythmias comprising an amount of a compound according to claim 2 effective to treat cardiac arrhythmias together with one or more pharmaceutically acceptable excipients or diluents.

26. A composition for treating cardiac arrhythmias comprising an amount of a compound according to claim 11 effective to treat cardiac arrhythmias together with one or more pharmaceutically acceptable excipients or diluents.

27. A composition for treating cardiac arrhythmias comprising an amount of N-[3-(diethylamino)propyl]-4,5-diphenyl-1H-pyrazole-1-acetamide or pharmaceutically acceptable acid addition salt thereof according to claim 12 effective to treat cardiac arrhythmias together with one or more pharmaceutically acceptable excipients or diluents.

28. A method for treating cardiac arrhythmias in a susceptible subject which comprises the step of administering an amount of a compound according to claim 1 effective to treat cardiac arrhythmias.

29. A method for treating cardiac arrhythmias in a susceptible subject which comprises the step of administering an amount of a compound according to claim 2 effective to treat cardiac arrhythmias.

30. A method for treating cardiac arrhythmias in a susceptible subject which comprises the step of administering an amount of a compound according to claim 11 effective to treat cardiac arrhythmias.

31. A method for treating cardiac arrhythmias in a susceptible subject which comprises the step of administering an amount of N-[3-(diethylamino)propyl]-4,5-diphenyl-1H-pyrazole-1-acetamide or pharmaceutically acceptable acid addition salt thereof according to claim 12 effective to treat cardiac arrhythmias.

* * * * *

UNITED STATES PATENT AND TRADEMARK OFFICE
CERTIFICATE OF CORRECTION

PATENT NO. : 4,870,095

DATED : September 26, 1989

INVENTOR(S) : Denis Mahlon Bailey

It is certified that error appears in the above-identified patent and that said Letters Patent is hereby corrected as shown below:

Column 13, line 43: "3.33 mL" should read --- 33.3 mL ---.

Column 15, line 29: "lacetamide" should read --- 1-acetamide ---.

Column 17, line 4: "tostand" should read --- to stand ---.

Column 17, line 14: "lacetamide" should read --- 1-acetamide ---.

Column 17, line 16: "(0.375 mL)" should read --- (0.375 mol) ---.

Column 18, line 26: "sat" should read --- salt ---.

Column 18, line 36: "filtered" should read --- filtering ---.

Column 22, line 4: "phenyl]4" should read --- phenyl]-4- ---.

Column 22, line 36: ")butyl]5" should read --- )butyl]-5 ---.

Column 22, line 41: "-62-" should read --- -β- ---.

Column 23, line 63: "VTAH" should read --- VTACH ---.

Column 27, line 12: "-1-H-" should read --- -1H- ---.

Column 2, line 62: "processar" should read --- processes ---.

Column 5, line 56: "N-[-hydroxyalkyl" should read --- N-[ω-hydroxyalkyl ---.

Column 7, line 41: "benefical" should read --- beneficial ---.

UNITED STATES PATENT AND TRADEMARK OFFICE
CERTIFICATE OF CORRECTION

PATENT NO. : 4,870,095
DATED : September 26, 1989
INVENTOR(S) : Denis Mahlon Bailey It is certified that error appears in the above-identified patent and that said Letters Patent is hereby corrected as shown below:

Column 10, line 12: "hydrazino acetate" should read --- hydrazinoacetate ---.

Column 10, line 62: "hydrazino-acetate" should read --- hydrazinoacetate ---.

Column 13, line 32: "N([6-" should read --- N-[6- ---.

Column 14, line 19: "]1H" should read --- 1H ---.

Column 16, line 22: "(0.065)mol)" should read --- (0.065 mol) ---.

Column 16, line 39: "colled" should read --- cooled ---.

Column 16, line 43: "N-[2-diethylamino)" should read --- N-[2-(diethylamino) ---.

Column 17, line 13: "83 6" should read --- 83.6 ---.

Column 19, line 27: "(00.33 mol)" should read --- (0.033 mol) ---.

Column 21, line 34: "8 1g" should read --- 8.1 g ---.

UNITED STATES PATENT AND TRADEMARK OFFICE
CERTIFICATE OF CORRECTION

PATENT NO. : 4,870,095

DATED : September 26, 1989

INVENTOR(S) : Denis Mahlon Bailey

It is certified that error appears in the above-identified patent and that said Letters Patent is hereby corrected as shown below:

Column 22, line 61: "N-7" should read --- N-[7 ---.

Signed and Sealed this

Twenty-eighth Day of May, 1991

*Attest:*

HARRY F. MANBECK, JR.

*Attesting Officer*  *Commissioner of Patents and Trademarks*